United States Patent
Cortellini

(10) Patent No.: US 7,972,385 B2
(45) Date of Patent: Jul. 5, 2011

(54) PATCH FOR REPLACEMENT OF A PORTION OF BLADDER WALL FOLLOWING PARTIAL CYSTECTOMY

(75) Inventor: Pietro Cortellini, Parma (IT)

(73) Assignee: Antonio Sambusseti, Cremona (IT)

( * ) Notice: Subject to any disclaimer, the term of this patent is extended or adjusted under 35 U.S.C. 154(b) by 486 days.

(21) Appl. No.: 12/088,888

(22) PCT Filed: Sep. 25, 2006

(86) PCT No.: PCT/EP2006/009274
§ 371 (c)(1),
(2), (4) Date: Jul. 8, 2008

(87) PCT Pub. No.: WO2007/039160
PCT Pub. Date: Apr. 12, 2007

(65) Prior Publication Data
US 2008/0319460 A1   Dec. 25, 2008

(30) Foreign Application Priority Data
Oct. 3, 2005   (IT) .............. MI2005A1854

(51) Int. Cl.
*A61F 2/02*   (2006.01)
*A61F 2/00*   (2006.01)
*A61F 13/00*  (2006.01)

(52) U.S. Cl. .............. 623/23.72; 600/37; 424/422

(58) Field of Classification Search .......... 606/151, 606/213; 623/23.72, 23.74, 23.65, 23.66; 602/41–61; 600/37; 128/99.1, 95.1; 424/422, 424/423, 424, 430
See application file for complete search history.

(56) References Cited

U.S. PATENT DOCUMENTS

| | | | | |
|---|---|---|---|---|
| 3,562,820 A * | 2/1971 | Braun | ......... | 623/23.64 |
| 3,824,996 A * | 7/1974 | Carlisle | ......... | 602/43 |
| 3,867,728 A * | 2/1975 | Stubstad et al. | ......... | 623/17.16 |
| 4,034,751 A * | 7/1977 | Hung | ......... | 602/52 |
| 4,051,848 A * | 10/1977 | Levine | ......... | 604/304 |
| 4,854,316 A * | 8/1989 | Davis | ......... | 606/153 |
| 5,000,172 A * | 3/1991 | Ward | ......... | 602/52 |
| 5,628,788 A * | 5/1997 | Pinchuk | ......... | 623/1.2 |
| 5,711,960 A * | 1/1998 | Shikinami | ......... | 424/426 |

(Continued)

FOREIGN PATENT DOCUMENTS
WO   95/11637 A   5/1995
(Continued)

OTHER PUBLICATIONS

Louis Asilkar et al., "The Silastio Bladder Patch", December, pp. 679-683.

*Primary Examiner* — Darwin P Erezo
*Assistant Examiner* — Dianne Dornbusch
(74) *Attorney, Agent, or Firm* — Young & Thompson

(57) ABSTRACT

A patch for replacement of a portion of bladder wall following partial cystectomy includes a multi-layered membrane of soft silicone with a thickness of about 600 microns so as to be sufficiently elastic to be able to withstand the dilatations due to expansion and deflation of the bladder, a surface layer of texturized silicone that is arranged to face an outside of a bladder to reduce a risk of adhesion of fibrotic capsule, and an inner coating of pyrolytic turbostatic carbon that is arranged to face an inside of the bladder.

7 Claims, 2 Drawing Sheets

U.S. PATENT DOCUMENTS

| | | | | |
|---|---|---|---|---|
| 5,733,337 | A * | 3/1998 | Carr et al. | 435/325 |
| 6,075,180 | A * | 6/2000 | Sharber et al. | 623/11.11 |
| 6,143,675 | A * | 11/2000 | McCollam et al. | 442/221 |
| 6,884,428 | B2 * | 4/2005 | Binette et al. | 424/422 |
| 7,160,333 | B2 * | 1/2007 | Plouhar et al. | 623/23.72 |
| 7,341,601 | B2 * | 3/2008 | Eisermann et al. | 623/17.11 |
| 2002/0028980 | A1 * | 3/2002 | Thierfelder et al. | 600/37 |
| 2002/0120348 | A1 * | 8/2002 | Melican et al. | 623/23.72 |
| 2003/0065402 | A1 * | 4/2003 | Anderson et al. | 623/23.66 |
| 2003/0125604 | A1 * | 7/2003 | Kochamba et al. | 600/37 |
| 2003/0147935 | A1 * | 8/2003 | Binette et al. | 424/423 |
| 2003/0212460 | A1 * | 11/2003 | Darois et al. | 623/23.64 |
| 2003/0225355 | A1 * | 12/2003 | Butler | 602/48 |
| 2004/0018228 | A1 * | 1/2004 | Fischell et al. | 424/450 |
| 2004/0236416 | A1 * | 11/2004 | Falotico | 623/1.42 |
| 2005/0096499 | A1 * | 5/2005 | Li et al. | 600/37 |
| 2005/0112397 | A1 * | 5/2005 | Rolfe et al. | 428/593 |
| 2005/0158274 | A1 * | 7/2005 | Hunter et al. | 424/78.38 |
| 2005/0216094 | A1 * | 9/2005 | Prewett | 623/23.74 |
| 2006/0229735 | A1 * | 10/2006 | Roy et al. | 623/23.74 |
| 2009/0117170 | A1 * | 5/2009 | Kroehne et al. | 424/424 |

FOREIGN PATENT DOCUMENTS

| | | |
|---|---|---|
| WO | 98/36707 A | 8/1998 |
| WO | 99/22781 A | 5/1999 |

* cited by examiner

PATCH FOR REPLACEMENT OF A PORTION OF BLADDER WALL FOLLOWING PARTIAL CYSTECTOMY

BACKGROUND OF THE INVENTION

The present invention refers to a patch for replacement of a portion of bladder wall, following partial cystectomy.

As is known, when a portion of a patient's bladder is affected by a serious pathology, such as partial malignancy, this portion of bladder must be removed to prevent the disease from spreading to the whole bladder. Removal of this portion of bladder creates a hole in the bladder which is closed by means of a patch sutured to the perimeter of the bladder wall defining this hole.

These patches are taken from the patient's bowel turned inside out. That is to say, during surgery the portion of bladder affected by the malignancy is removed, Then, a patch is removed obtained by cutting the patient's bowel wall in situ, taking care to wash and clean it carefully to eliminate any source of infection, due above all to the intestinal mucus. Finally, this patch is sutured to the bladder wall to close the hole left by removal.

This system nevertheless presents some drawbacks. In fact during surgery it is not possible to eliminate the intestinal mucus entirely from the new bladder, resulting in possible infections.

Furthermore these patches of bowel wall have a short average life. In fact they are unable to go beyond a life of 10 years because of tearing of the intestinal wall which wears out in a period of less than 2-3 years.

Various attempts to produce synthetic patches have not been successful, mainly because the inner surface of the patch did not withstand encrustation from urine.

SUMMARY OF THE INVENTION

Object of the present invention is to overcome the drawbacks of the prior art, by providing a patch for replacement of a portion of bladder wall following partial cystectomy which is reliable and long-lasting.

Yet another object of the present invention is to provide such a patch that is practical for the surgeon and at the same time easy to produce.

The patch for replacement of a portion of bladder wall following partial cystectomy according to the invention comprises a multi-layered membrane of soft silicone with a thickness of about 600 microns.

In this manner the patch is sufficiently elastic to be able to withstand dilatations due to expansion and deflation of the bladder.

BRIEF DESCRIPTION OF THE DRAWINGS

Further characteristics of the invention will be made clearer by the detailed description that follows, referring to purely exemplifying and therefore non limiting embodiments thereof, illustrated in the appended drawings, in which.

DESCRIPTION OF PREFERRED EMBODIMENTS

Figure 1:
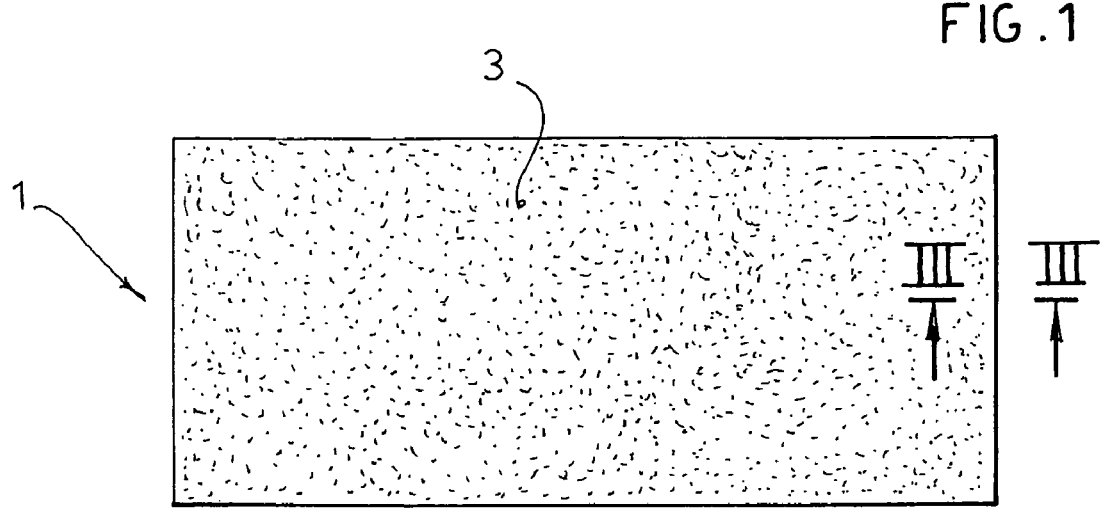
FIG. 1 is a plan view of a patch according to a first embodiment of the invention, shown from the side destined to face towards the outside of the bladder.
Figure 2:
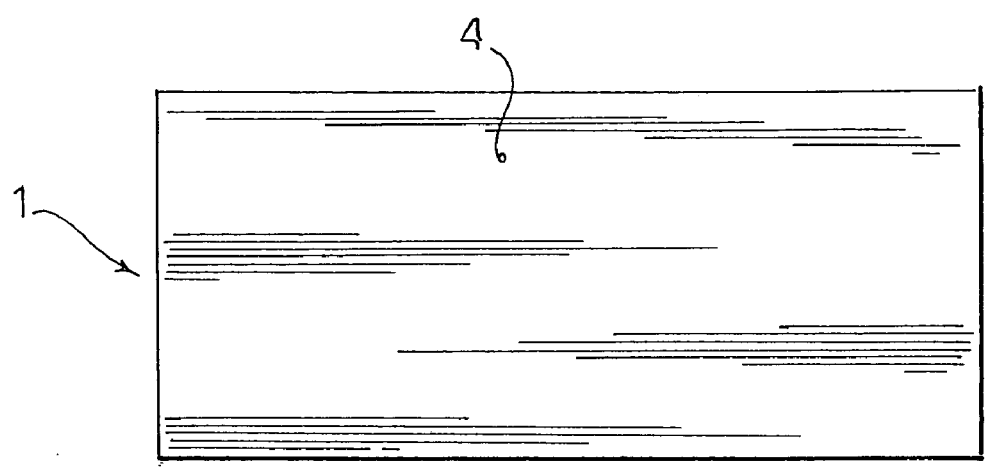
FIG. 2 is a plan view of the patch of FIG. 1, but shown from the side destined to face towards the inside of the bladder.
Figure 3:
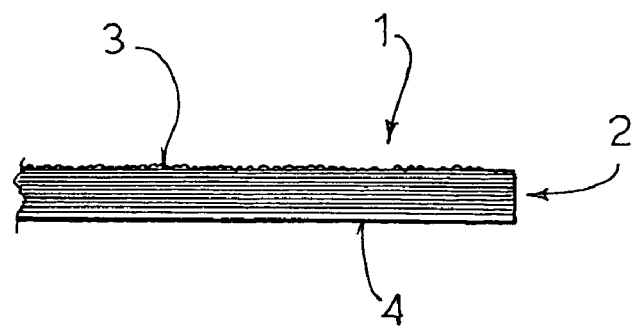
FIG. 3 is an enlarged cross sectional view of a portion of the patch, in which the section is taken along the sectional plane III-III of FIG. 1.

With reference for now to FIGS. 1-3 a patch according to the first embodiment of the invention, denoted as a whole with reference number 1, is described. The patch 1 is made from a multi-layered membrane (FIG. 3) of soft silicone, with a thickness of about 600 microns so as to be sufficiently elastic to be able to withstand the dilations due to expansion and deflation of the bladder.

The silicone used, for example, may be made of copolymers of dimethyl and metavinyl siloxane, reinforced with silica or silicon. A medical silicone is preferably used, such as for example that known by the code number MED 4735™ and marketed by Nusil Technology.

The membrane 2 of the prosthesis 1 preferably consists of 20 layers of silicone, each with a thickness of about 30 microns.

The layers of silicone are overlapped in the semi liquid state and then the layered membrane 2 is placed in an oven for vulcanisation at a temperature of about 150° C. and for a time ranging from 30 min to 1 h, according to the size of the patch that is to be produced. After the vulcanisation cycle, the multi-layered silicone membrane is in its optimal consistency of softness and elasticity and is no longer in the semi-liquid state.

The last, outermost layer 3 of the silicone membrane, destined to face towards the outside of the bladder, is advantageously texturised so as to obtain a rough surface which serves to minimize the risk of adhesion of the fibrotic capsule to the patch 1. The texturising process involves only the last outer layer 3. Once the last layer of silicone 3 has been applied, it is evaporated with cyclohexane for 10 minutes and is sprinkled with normal cooking salt (NaCl) before vulcanization. The silicone membrane 2 with the salted final layer 3 is then placed in the oven for vulcanization.

This procedure of salting of the last layer 3 and vulcanization is repeated twice. At the end of the two cycles of salting and vulcanization, the final device is dipped into water and brushed to eliminate the salt from the last layer 3.

The surface of the patch 1 destined to face towards the inside of the bladder is coated with a microfilm 4 of highly biocompatible biomaterial, such as for example pyrolytic turbostratic carbon, having a thickness of about 0.2-0.3 microns.

Experimental laboratory and bench tests with a scanning electron microscope have been performed on samples of silicone strips coated with such a biomaterial. These samples were dipped into human urine for one week and subjected to torsion, bending and folding stress for cycles of 10,000 times. Microscope scanning did not yield any sign of deterioration due to the corrosive effect of urine.

Figure 4:
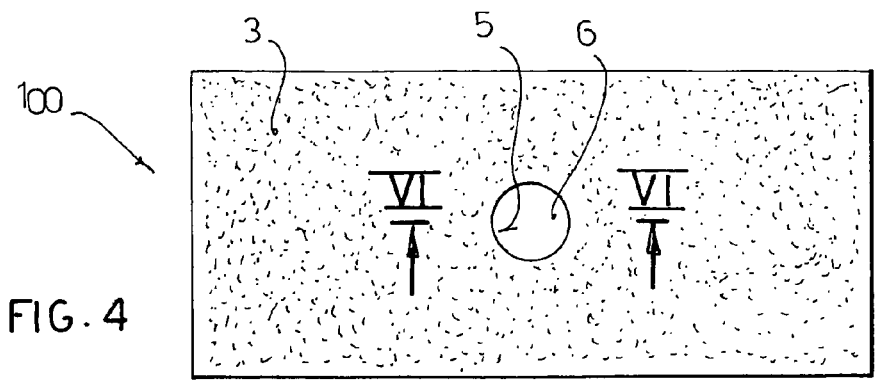
FIG. 4 is a plan view, partially cut away, of a patch according to a second embodiment of the invention, shown from the side destined to face towards the outside of the bladder.
Figure 5:
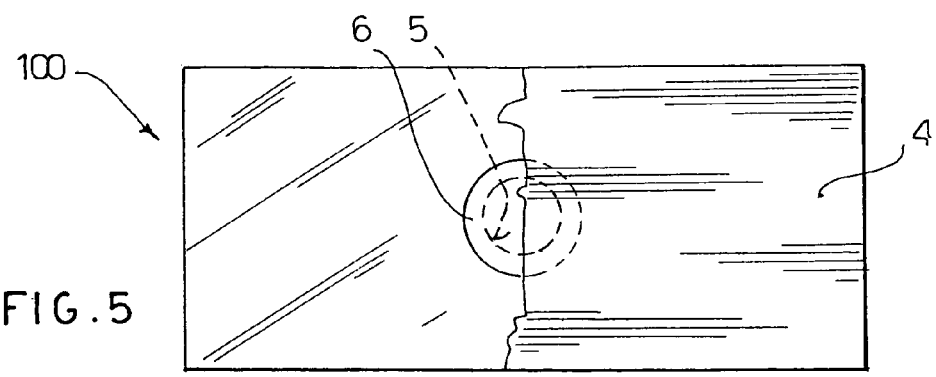
FIG. 5 is a plan view of the patch of FIG. 4, but shown from the side destined to face towards the inside of the bladder.
Figure 6:
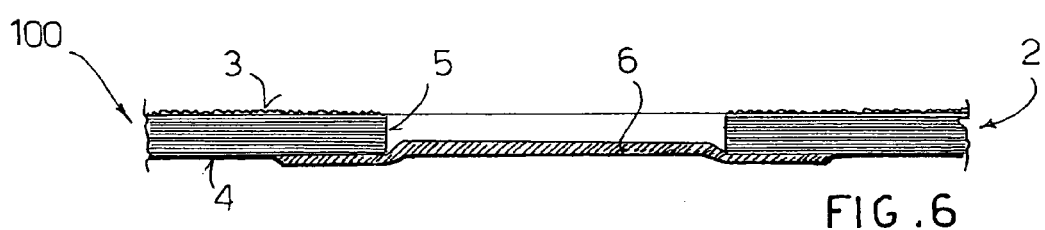
FIG. 6 is an enlarged cross sectional view of a portion of the patch, in which the section has been taken along the sectional plane VI-VI of FIG. 4.

With reference to FIGS. 4-6 a patch 100 according to a second embodiment of the invention is described, in which like or corresponding elements to those already described are indicated with the same reference numerals and are not described in detail.

Figure 7:
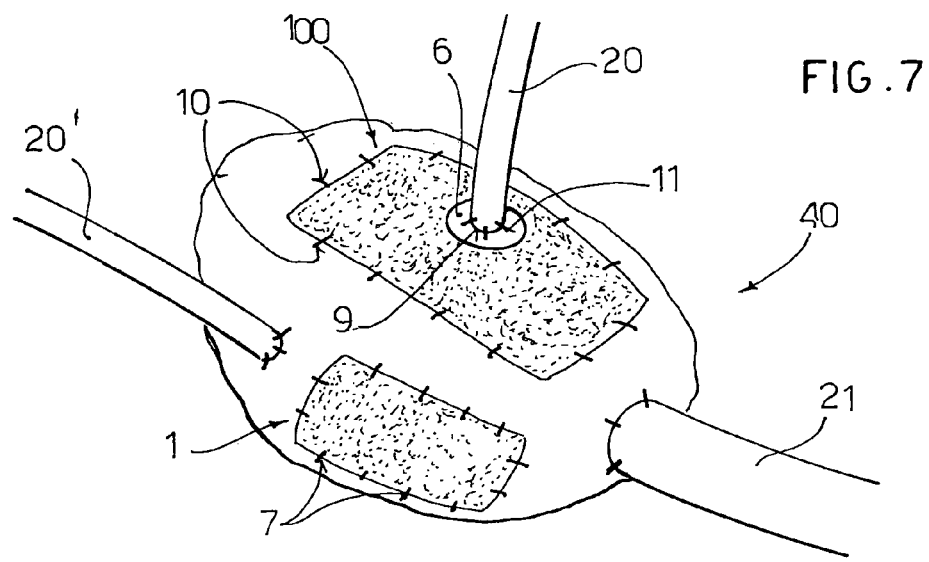
FIG. 7 is a perspective view, illustrating diagrammatically the application of the patches according to the first and second embodiment of the invention to a bladder.

In this case the patch 100 has a multi-layered membrane 2 of soft silicone provided with a hole 5 having a larger diameter than the diameter of the ureters 20, 20' and of the urethra 21 (shown in FIG. 7). This hole 5 can have a diameter of 20 mm.

The hole 5 is made with a special surgical instrument consisting of a handpiece or punch, with a squared section tip 3 cm long and a final diameter between 8 and 14 charrrier (Ch), to comply with the possible dimensions of the ureters 20, 20' and the urethra 21.

The hole 5 is closed by a portion of membrane 6 with a substantially discoid shape and a larger diameter than the hole 5. The portion of membrane 6 is similar to the multi-layered membrane 2 but can be without the texturized layer on the outer surface. The portion of membrane 6 is applied to the inner surface of the patch 100 destined to face towards the inside of the bladder, by means of melting or heat bonding of the silicones in a single layer with the membrane 2, and subsequent vulcanization in an oven.

Finally the inner surface of the patch 100, together with the portion of membrane 6, are coated with the microfilm of pyrolytic turbostratic carbon 4.

The patches 1 and 100 can be produced in any shape and size. The patches 1 and 100 can preferably have a rectangular shape 200 mm×300 mm or a square shape with a 200 mm side.

For both patches 1 and 100 the whole manufacturing cycle must be performed in a controlled atmosphere, that is with controlled contamination, in a white room. Once processing is completed, the patches 1, 100 are placed in a double blister pack closed with a sheet of Tyvek to avoid contamination, and sent for an ETO (ethylene oxide) sterilization cycle.

At this point the patches 1, 100 are ready to be used during a surgical session.

FIG. 7 shows diagrammatically a bladder 40 with the relative ureters 20, 20' and urethra 21.

If the area of the bladder 40 affected by malignancy is distant from the ureters 20, 20' e urethra 21, the surgeon removes this affected area and applies a patch 1 to cover the removal hole by means of suture stitches 7 which connect the perimeter of the patch 1 to the bladder wall 50 around the removal hole.

FIG. 7 also shows the case in which the area of the bladder 40 affected by malignancy is near one 20 of the ureters. In this case the surgeon removes said affected area detaching it from the relative ureter 20.

Then, the surgeon makes a hole 9 in the portion of membrane 6 of the patch 100. In order to pierce the portion of membrane 6, the surgeon can use the same hand piece or punch used to pierce the membrane 2 during production of the patch 100. The tip of the punch is chosen according to the size of the ureter 20 and the hole 9 is made with the Ch measurement that the surgeon considers appropriate according to the size of the ureter 20 during the surgical procedure.

The ureter 20 is inserted into the hole 9 of the patch 100, which, being elastic, tightens slightly around the tube of the ureter 20. Then, the portion of membrane 6 of the patch 100 is fixed to the ureter 20 by means of four suture stitches 11 disposed in a square, around the tube of the ureter 20 and passing through the portion of membrane 6 and through the tissue of the ureter 20.

Finally the perimeter of the patch 100 is fixed, by suture stitches 10, to the bladder wall 40 around the ureter 20.

For example, for the suture stitches 7, 11 and 10 a curved cylindrical needle must be used and Monocryl Ethicon™ 4-0 e 5-0 thread can be used, produced by Johnson & Johnson and consisting of polyglecaprone, that is: a copolymer made by synthesis of glycolide (75%) and epsilon caprolactone (25%). This thread is not coated, is monofilament and is not braided. The manufacturer indicates this thread as the most suitable for sutures in general for soft tissue and vessels, amongst which are included the ureters and urethra.

There are, however, other suture materials which could conveniently be adapted to the cases in question and to the requirements of the patches; it is left to the surgeon's discretion to choose the one most congenial to him.

The holes for passage of the suture stitches 7, 11 and 10 in the ureter 20 and in the bladder 40 do not constitute a risk of leakage of liquid, in that in a few hours the tissue reforms. In order to avoid leakage of urine (liquid) the holes of the suture stitches 7, 11 and 10 are bonded and closed with one cc (one drop) of surgical glue, such as Glubran 2™ for example, normally available on the market.

The Monocryl™ thread used for the suture stitches is absorbed in about 90-120 days, but begins its downward curve of loss of tension on the 22nd day, ending and losing 75% of its tensile strength on the 28th day. From the 28th day tensile strength is no longer present in the thread, but by this date the ureter 20 and the patches 1 and 100 are kept fixed by the glue and above all by the formation of the fibrotic capsule which acts as a retaining element for the ureter and the patches 1 and 100. It should be noted that the fibrotic or polyproteic capsule forms in about 30 days.

Numerous changes and modifications of detail within the reach of a person skilled in the art can be made to the present embodiment of the invention, without thereby departing from the scope of the invention as set forth in the appended claims.

The invention claimed is:

1. A patch for replacement of a portion of bladder wall following partial cystectomy, the patch comprising:
   a multi-layered membrane of soft silicone the multi-layered membrane having a thickness of 600 microns so as to be sufficiently elastic to be able to withstand dilations due to expansion and deflation of the bladder,
   said multi-layered membrane comprising 20 layers of silicone placed on top of each other, each of said layers having a thickness of 30 microns,
   a surface layer of texturized silicone that is arranged to face an outside of a bladder to reduce a risk of adhesion of a fibrotic capsule, and
   an inner coating of pyrolytic turbostratic carbon that is arranged to face an inside of the bladder.

2. The patch according to claim 1, wherein said 20 layers of silicone are overlapped, vulcanized layers of silicone.

3. The patch according to claim 1, wherein said 20 layers of silicone of the multi-layered membrane consist of copolymers of dimethyl and metavinyl siloxane, reinforced with silicone.

4. The patch according to claim 3, wherein said 20 layers of silicone comprise a silicone for medical use.

5. The patch according to claim 1, wherein said inner coating is a microfilm with a thickness of 0.2-0.3 microns.

6. The patch according to claim 1, further comprising a hole with a larger diameter than the diameter of the ureters and of the urethra, said hole being covered by a portion of silicone membrane heat bonded to said multi-layered membrane.

7. The patch according to claim 6, wherein said portion of silicone membrane has the same structure and is made of the same material as said multi-layered membrane and is not provided with said surface layer of texturized silicone.

* * * * *